United States Patent [19]
Becker et al.

[11] Patent Number: 5,612,366
[45] Date of Patent: Mar. 18, 1997

[54] NEW MESO-AZACYCLIC AROMATIC ACID AMIDES AND ESTERS AS NOVEL SEROTONERGIC AGENTS

[75] Inventors: Daniel P. Becker, Glenview; Daniel L. Flynn, Mundelein; Alan E. Moorman, Skokie; Roger Nosal, Buffalo Grove; Clara I. Villamil, Glenview, all of Ill.

[73] Assignee: G. D. Searle & Co., Chicago, Ill.

[21] Appl. No.: 234,336

[22] Filed: Apr. 28, 1994

Related U.S. Application Data

[60] Division of Ser. No. 973,090, filed as PCT/US92/01525, Mar. 4, 1992, Pat. No. 5,318,977, which is a continuation-in-part of Ser. No. 666,151, Mar. 7, 1991, abandoned.

[51] Int. Cl.$^6$ .......................... A01K 31/40; C07D 487/04
[52] U.S. Cl. .......................................... 514/413; 548/453
[58] Field of Search ............................ 548/453; 514/413

[56] References Cited

U.S. PATENT DOCUMENTS

| | | | |
|---|---|---|---|
| 4,213,983 | 7/1980 | Hadley et al. | 546/94 |
| 4,273,778 | 6/1981 | Hadley et al. | 514/304 |
| 4,336,259 | 6/1982 | Hadley et al. | 514/299 |
| 4,409,225 | 10/1983 | Hadley et al. | 424/256 |
| 4,564,624 | 1/1986 | Miyano et al. | 548/453 |
| 4,617,401 | 10/1986 | Miyano et al. | 548/453 |
| 4,797,387 | 1/1989 | King | 514/212 |
| 4,797,406 | 1/1989 | Richardson et al. | 514/299 |
| 4,816,453 | 3/1989 | Watts | 514/217 |
| 4,826,838 | 5/1989 | Richardson et al. | 546/94 |
| 5,137,893 | 8/1992 | Becker et al. | 514/214 |
| 5,140,023 | 8/1992 | Becker et al. | 514/214 |
| 5,196,547 | 3/1993 | Becker et al. | 548/453 |
| 5,219,850 | 6/1993 | Becker et al. | 514/214 |
| 5,227,377 | 7/1993 | Flynn et al. | 514/214 |
| 5,234,921 | 8/1993 | Flynn et al. | 514/214 |

FOREIGN PATENT DOCUMENTS

| | | | |
|---|---|---|---|
| 12496/83 | 9/1983 | Australia | C07D 451/14 |
| 67121/87 | 7/1987 | Australia | C07D 451/04 |
| 0076592 | 4/1983 | European Pat. Off. | C07D 451/15 |
| 094742 | 11/1983 | European Pat. Off. | C07D 451/14 |
| 0189002 | 7/1986 | European Pat. Off. | A61K 31/445 |
| 0201165 | 11/1986 | European Pat. Off. | A01K 31/40 |
| 0220011 | 4/1987 | European Pat. Off. | A61K 31/435 |
| 0230718 | 6/1987 | European Pat. Off. | C07D 211/58 |
| 0315390 | 5/1989 | European Pat. Off. | C07D 451/04 |
| 0323077 | 7/1989 | European Pat. Off. | C07D 451/04 |
| 2152049 | 7/1985 | United Kingdom | C07D 451/14 |
| 2166726 | 5/1986 | United Kingdom | C07D 453/02 |
| 2169292 | 7/1986 | United Kingdom . | |

OTHER PUBLICATIONS

Fludzinski et al. "Indazoles as Indole Biosteres," J. Med. Chem. 30(() 1535–1537 (1987).
Miyano et al. "Synthesis of 7a–Substituted . . . Pyrrolizines . . . " J. Pharm. Sci., vol. 76, No. 5, pp. 416–418 (1987).
Yatani et al. "Effects of New Antiarrhythmic Compound SUN 1165 . . . " Nauyn–Schmiedeberg's Arch. Pharmacol., vol. 326, pp. 163–168 (1984).

*Primary Examiner*—Robert Gerstl
*Attorney, Agent, or Firm*—Cynthia S. Kovacevic; Roger A. Williams

[57] ABSTRACT

The meso-azacyclic aromatic acid amides and esters of the present invention are useful in the treatment of the central nervous system and gastrointestinal motility disorders such as gastroesophageal reflux, non-ulcer dyspepsia, delayed gastric emptying, ileus, irritable bowel syndrome, and the like. Additionally, the compounds of the present invention find utility as antagonists of serotonin 5-HT$_3$ receptors. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and/or withdrawal, irritable bowel syndrome, emesis caused by chemotherapeutic agents, and visceral pain. Additionally, the compounds of the present invention may find utility as enhancers of nasal absorption of bioactive compounds.

2 Claims, No Drawings

NEW MESO-AZACYCLIC AROMATIC ACID AMIDES AND ESTERS AS NOVEL SEROTONERGIC AGENTS

This is a divisional application of U.S. Ser. No. 07/973, 090, filed Nov. 6, 1992, now allowed, which is a continuation of International Application Serial No. US92/01525 filed on Mar. 4, 1992, which was a continuation-in-part application of U.S. Ser. No. 07/666,151, filed Mar. 7, 1991, now abandoned.

BACKGROUND OF THE INVENTION

The invention herein is directed to compounds and a method of treating gastrointestinal motility disorders of a mammal by administering to the mammal in need thereof a therapeutically effective amount of a compound disclosed herein or a pharmaceutically acceptable salt thereof. The method can be practiced to treat gastrointestinal motility disorders such as gastroesophageal reflux, diseases characterized by delayed gastric emptying, ileus, irritable bowel syndrome, and the like. The compounds of the invention are serotonergic 5-$HT_3$ antagonists and as such are useful for the treatment of conditions, for example, such as anxiety, psychoses and depression.

There are classes of compounds known for the treatment of such disorders. For example, azatetracycle compounds are disclosed in co-pending U.S. patent application Ser. No. 07/515,391 filed Apr. 27, 1990, and N-Azabicyclo [3.3.0] octane amides of aromatic acids are disclosed in copending application Ser. No. 07/406,205 filed Sep. 11, 1989.

Aza-adamantyl compounds are disclosed in U.S. Pat. No. 4,816,453 and are mentioned generically in U.K. Patent 2,152,049A and European application 0189002A2.

Azabicyclic nonanes are disclosed in European Patent application 0094742A2. Additional azabicyclic compounds are disclosed in U.S. Pat. Nos. 4,797,387 and 4,797,406.

Benzamides have been known as 5-$HT_3$ antagonists and as compounds possessing gastrointestinal motility-enhancing properties. Benzamides of the following formula:

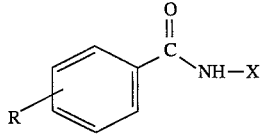

compounds wherein X can be an azabicycloalkane moiety and which exhibit gastrointestinal motility enhancing and/or 5-$HT_3$ antagonist properties are disclosed in EP 0094742A2 and in U.S. Pat. No. 4,797,406. In addition, UK Patent 2,152,049 discloses that certain benzamide derivatives exhibit serotonin M antagonistic activity.

Indoleamides of the following formula have also been described as possessing gastrointestinal motility-enhancing and/or 5-$HT_3$ antagonist properties:

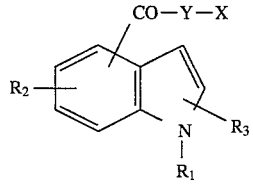

Compounds wherein X contains an aminergic side chain or an azabicycloalkane moiety are described in U.S. Pat. No. 4,797,406.

European patent publication number 0,230,718 discloses certain substituted benzamide derivatives, substituted with piperidinyl analogues as having gastrointestinal motility-enhancing and/or antiemetic activity and/or 5-HT receptor antagonist activity. *J. Heterocyclic Chemistry* (1987) 24:47 describes the preparation of the following compound: No substitution is shown in the phenyl ring and no utility is described.

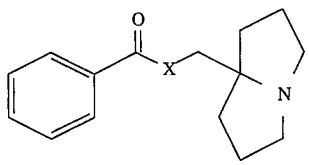

X = O, NH

*J. Pharmaceutical Sciences* (1987) 76:416 describes compounds of generic scope. Utility as anti-arrhythmic agents is described.

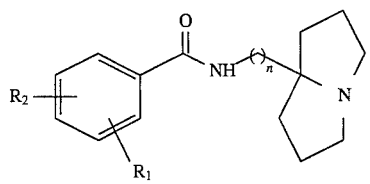

n=1 or 2
$R_1$=H, 2-Me, 4-$NH_2$, 4-OMe, 4-$NHCO_2Et$, 2-OEt, 4-OEt, 3- or
4-$NMe_2$, 3- or 4-$NO_2$; $R_2$=H or 6-Me.

JP Patent 58083694 A2 and JP 0027355B describe anti-arrhythmic agents of the following formula wherein n=1 or 2; $R_1$ or $R_2$ are both Me or $R_1$ is H while $R_2$ is nitro, di-lower alkylamino, lower alkoxycarbonylamino, or ethoxy.

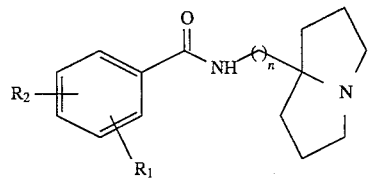

EP Patent 39,903 and U.S. Pat. No. 4,617,401 describe compounds of the following formula wherein R is H, OMe, OH, or $NH_2$; X is NH or O; and Z is a lone electron pair or optionally substituted alkyl group. The compounds are described as spasmolytic, antiarrhythmic, and neuromuscular-blocking agents.

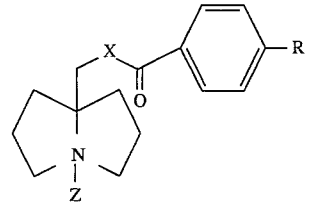

SUMMARY OF THE INVENTION

The compounds of the present invention are useful in the treatment of gastrointestinal motility disorders such as gastroesophageal reflux, non-ulcer dyspepsia, delayed gastric emptying, ileus, irritable bowel syndrome, and the like. Additionally, the compounds of the present invention find utility as antagonists of serotonin 5-HT$_3$ receptors. As such they are useful for the treatment of humans and animals wherein antagonism of 5-HT$_3$ receptors is beneficial. Therapy is indicated for, but not limited to, the treatment of anxiety, psychoses, depression (especially depression accompanied by anxiety), cognitive disorders, substance abuse dependence and/or withdrawal, irritable bowel syndrome, emesis caused by chemotherapeutic agents, and visceral pain. Additionally, the compounds of the present invention may find utility as enhancers of nasal absorption of bioactive compounds.

DETAILED DESCRIPTION OF THE INVENTION

The invention herein is directed to compounds of formula I:

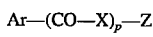

the stereoisomers and pharmaceutically acceptable salts thereof wherein p is 0 or 1 and when p is 0, Ar represents a radical of the formula:

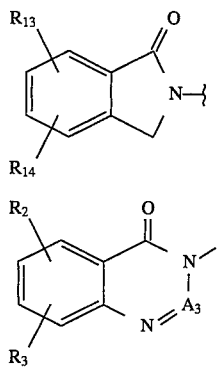

and when p is 1, Ar represents a radical of the formula:

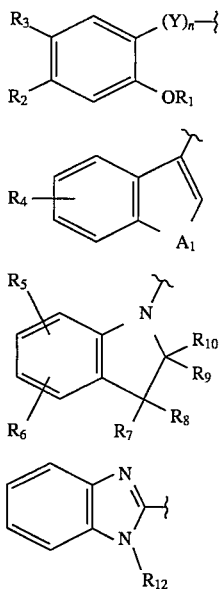

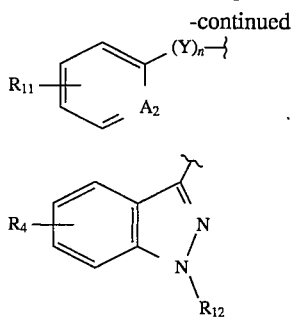

Wherein Y is NH; $R_1$ is $C_{1-6}$ alkoxy; $R_2$ and $R_3$ are independently H, halogen, $CF_3$, hydroxyl, $C_{1-2}$ alkoxy, $C_{2-7}$ acyl, amino, amino substituted by one or two $C_{1-6}$ alkyl groups, $C_{2-7}$ acylamino, aminocarbonyl, or aminosulfone optionally substituted by one or two $C_{1-6}$ alkyl groups, $C_{1-6}$ alkylsulfone, or nitro; $R_4$ is H, halo, or $C_{1-6}$ alkoxy; $R_5$ and $R_6$ are the same or different and can be H, halo, $CF_3$, $C_{1-6}$alkyl, $C_{1-6}$ alkoxy, $C_{1-6}$ alkylthio, $C_{1-7}$ acyl, $C_{1-7}$ acylamino, $C_{1-6}$ alkylsulfonylamino, N—($C_{1-6}$ alkylsulfonyl)-N—$C_{1-4}$ alkylamino, $C_{1-6}$ alkylsulfinyl, hydroxy, nitro, or amino, aminocarbonyl, aminosulfonyl, aminosulfonylamino, or N-(aminosulfonyl)-$C_{1-4}$ alkylamino optionally N'-substituted by one or two groups selected from $C_{1-6}$ alkyl, $C_{3-8}$ cycloalkyl, phenyl, or phenyl $C_{1-4}$ alkyl groups or optionally N'-disubstituted by $C_{4-5}$ polymethylene; $R_7$ and $R_{10}$ can be the same or different and can be H, $C_{1-6}$ alkyl, $C_{2-6}$ alkenyl, $C_{1-4}$ alkyl or together are $C_{2-4}$ polymethylene; $R_8$ and $R_9$ can be the same or different and can be H, $C_{1-4}$ alkyl or taken together are a covalent bond; $R_{11}$ is H or halogen; $R_{12}$ and $R_{12}'$ are the same or different and can be H, $C_{1-6}$ alkyl, or phenyl $C_{1-4}$ alkyl; $R_{13}$ and $R_{14}$ can be the same or different and can be H, halo, $CF_3$, $C_{1-6}$ alkyl, $C_{1-7}$ acyl, $C_{1-7}$ acylamino, or amino, aminocarbonyl or aminosulfonyl, optionally substituted by one or two $C_{1-6}$ alkyl or $C_{3-8}$ cycloalkyl groups, or by $C_{4-5}$ polymethylene or biphenyl, $C_{1-6}$ alkylsulfonyl, $C_{1-6}$ alkylsulfinyl, $C_{1-6}$ alkoxy, $C_{1-6}$ alkylthio, hydroxy, or nitro, or when $R_{13}$ and $R_{14}$ are taken together are methylenedioxy or ethylenedioxy; $A_1$ is O, S, N($R_{12}$), or $CH_2$; $A_2$ is C—$OR_{12}$, N+—O—, $CO_2R_{12}$, $CONR_{12}(R_{12}')$, $SR_{12}$, or $SO_2NR_{12}(R_{12}')$; $A_3$ is N or CH; X is NH or O; and Z represents a radical of the formula:

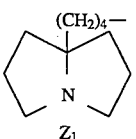

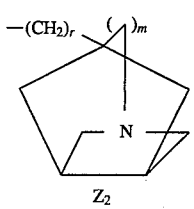

Wherein m is 1 or 2, n is 0 or 1, p is 1 or 2, q is 1 or 2, and r is 0 or 1.

The term "cycloalkyl" embraces cyclic radicals having three to about ten ring carbon atoms, preferably three to about six carbon atoms, such as cyclopropyl and cyclobutyl. The terms "alkoxy" and "alkoxyalkyl" embrace linear or branched oxy-containing radicals each having alkyl portions of one to about ten carbon atoms, such as methoxy group.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neopentyl.

Included within the family of compounds of the described are the tautomeric forms of the described compounds, isomeric forms including diastereoisomers and individual enantiomers, and the pharmaceutically-acceptable salts thereof. The term "pharmaceutically-acceptable salts" embraces salts commonly used to form alkali metal salts and to form addition salts of free acids or free bases. Since the compounds contain basic nitrogen atoms, such salts are typically acid addition salts. The phrase "pharmaceutically-acceptable salts" is intended to embrace alkyl quaternary ammonium salts and n-oxides. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of the invention.

The compounds that are the subject of the invention herein can be prepared according to the following reaction schemes.

$Z_1$ is known and is prepared as described by Miyano and coworkers [J. Heterocyclic Chemistry (1987) 24, 47 for q=1; J. Pharmaceutical Sciences (1987), 76, 416 & references sited therein]. $Z_2$ is prepared according to schemes 1, 2, and 3.

Scheme 1 describes the preparation of amino-azacycles $Z_2$. The BOC-amine 1 (U.S. Patent Application Ser. No. 07/515,391) is deprotected with trifluoroacetic acid and the resulting amine is cyclized intramolecularly with the exocyclic olefin by treatment with iodine and potassium iodide in the presence of sodium bicarbonate to yield the bridgehead iodide 2. Treatment of 2 with silver isocyanate affords the bridgehead isocyanate which may be hydrolyzed to give the requisite amine $Z_2$ wherein r=0. Alternatively treatment of 2 with silver cyanide affords the bridgehead nitrile which may be reduced to give the desired aminomethyl-azacycle $Z_2$ wherein r=1.

Scheme 2 illustrates the preparation of $Z_2$ hydroxy azacycles. Hydrolysis of bridgehead iodide 2 affords the desired hydroxy azacycle $Z_2$'' wherein r=0. Alternatively treatment of 2 with silver cyanade followed by hydrolysis and reduction gives the desired hydroxymethyl azacycle $Z_2$''' wherein r=1.

Scheme 3 illustrates the preparation of ethano-bridged azatricycles ($Z_2$'''', wherein m=2). The azabicycloketone 3 is converted first to its O-benzyloxime. Removal of the N-BOC protecting group, followed by acylation with chloroacetic anhydride & iodide exchange, affords the intermediate 4. Cyclization under reductive radical-cyclization conditions ($Bu_3SnH$, AIBN) affords the ethano-bridged lactam 5. Reduction with lithium aluminum hydride affords the desired ethano-bridged azatricycle $Z_2$''''.

Scheme 4 illustrates an alternative preparation of azacycle $Z_2$ (wherein r and m are each 1). The known 2(1,1-dimethylethyl)-5,5-dimethyl hexahydrocyclopenta[c]pyrrole-2,5,5-tricarboxylate 6 (Journal of Organic Chemistry, 1990, 55, 3673) is converted to the diol 7 by hydride reduction, preferably lithium borohydride in tetrahydrofuran. This diol is converted to a derivative 8 in which Q is a suitable leaving group (preferably tosylate: by reaction of the diol 7 with p-toluenesulfonyl chloride/pyridine). Deprotection of the N-butoxycarbonyl moiety by treatment with acid, preferably triflouroacetic acid, then affords the bis-tosylate amine 9. Reaction of 9 with a base, preferably cesium carbonate in dimethylformamide, gives the O-tosylated azatricycle 10. Reaction of 10 with sodium azide in a polar, aprotic solvent (preferably dimethylformamide or dimethylsulfoxide affords the azido-substituted azatricycle 11, which is subjected to reduction, preferably lithium aluminum hydride in tetrahydrofuran, to afford the desired amino-substituted azatricycle $Z_2$ (r=m=1).

SCHEME 1:
PREPARATION OF $Z_2$ AMINO-AZACYCLES

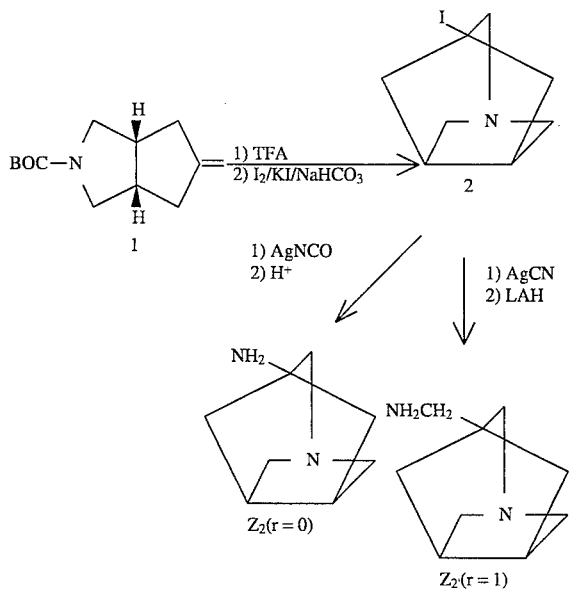

SCHEME 2:
PREPARATION OF $Z_2$ HYDROXY AZACYCLES

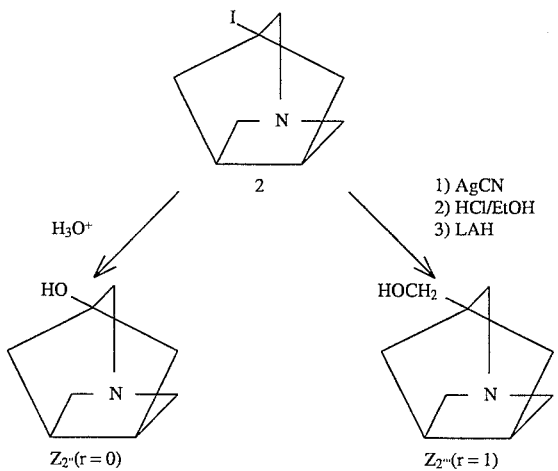

SCHEME 3: PREPARATION OF ETHANO-BRIDGED MESO-AZATRICYCLE

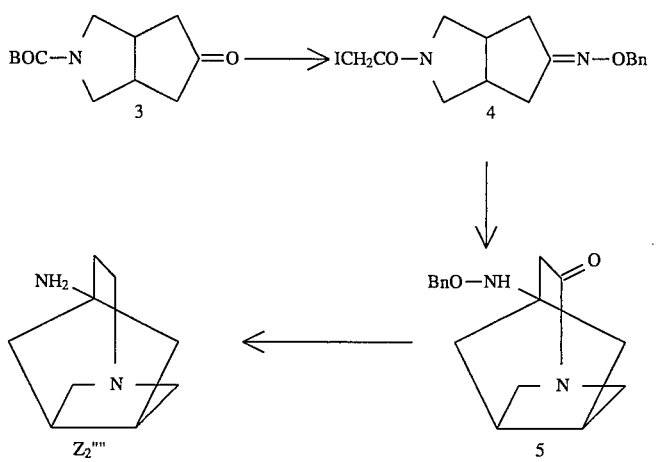

Scheme 4: Alternative Preparation of Z₂ Amino-Azacycle

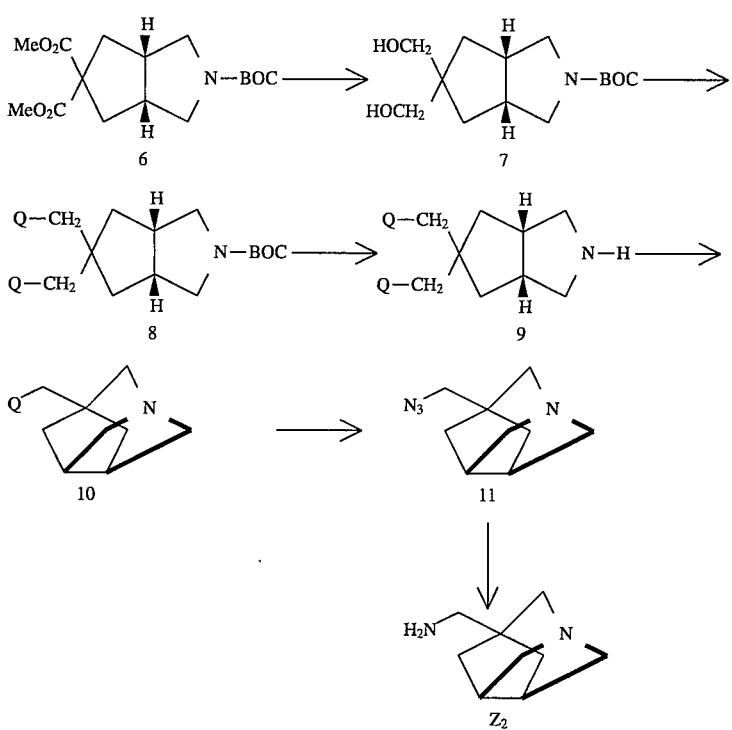

These examples, as well as all examples herein, are given by way of illustration only and are not to be construed as limiting the invention, either in spirit or scope, as many modifications, both in materials and methods, will be apparent from this disclosure to those skilled in the art. In these examples, temperatures are given in degrees Celsius (°C.) and quantities of materials in grams and milliliters unless otherwise noted.

EXPERIMENTALS

Example A

Preparation of hexahydro-5-iodo-2,5β-methano-1H-3aα, 6aα-cyclopenta[c]pyrrole

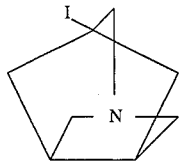

Cis-N-t-butoxycarbonylhexahydro-5-methylenecyclopenta[c]pyrrole [See co-pending application Ser. No. 07/515,391 filed Apr. 27, 1990] is treated with trifluoroacetic acid to afford an intermediate trifluoroacetate ammonium salt, which is then treated with base and $I_2$ to afford the title compound.

Example B

Preparation of tetrahydro-2,5β-methano-1H-3aα, 6aα-cyclopenta[c]pyrrol-5(3H)-amine

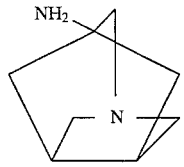

The iodo compound prepared in example A is treated with silver isocyanate to afford the intermediate N-formamide. This formamide is hydrolyzed to give the title compound.

Example C

Preparation of tetrahydro-2,5β-methano-1H-3aα, 6aα-cyclopenta[c]pyrrole-5(3H)-carbonitrile

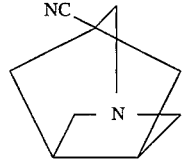

The iodo compound prepared in example A is treated with silver cyanide in dimethylformamide to afford the title compound.

Example D

Preparation of tetrahydro-2,5β-methano-1H-3aα, 6aα-cyclopenta[c]pyrrole-5(3H)-methanamine

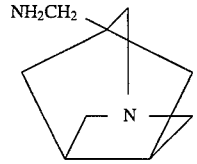

The nitrile compound prepared in example C is reduced with lithium aluminum hydride in etheral solvent to afford the title compound.

Example E

Preparation of tetrahydro-2,5β-methano-1H-3aα, 6aα-cyclopenta[c]pyrrole-5(3H)-methano

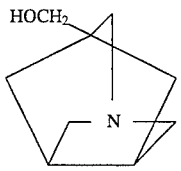

The nitrile compound prepared in example C is converted to the intermediate ethyl ester by treatment with aqueous ethanolic HCl. The ethyl ester is then treated with lithium aluminum hydride in etheral solvent to afford the title compound.

Example F

Preparation of 1,1-dimethylethyl hexahydro-5-[(phenylmethoxy)imino]cyclopenta[c]pyrrole-2(1H)-carboxylate

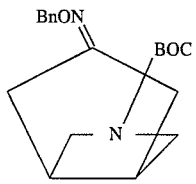

Cis-N-Butoxycarbonylhexahydro-5-oxo-cyclopenta[c]pyrrole is reacted with O-benzylhydroxylamine hydrochloride and sodium acetate in methanol to afford the title compound.

Example G

Preparation of octahydro-2-(iodoacetyl)-5-[(phenylmethoxy)imino]cyclopenta[c]pyrrole

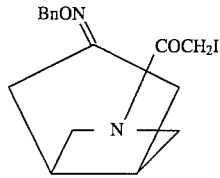

The title compound of example F is treated with trifluoroacetic acid in methylene chloride at room temperature. The volatiles are removed under reduced pressure to afford a residue which is treated with chloroacetic anhydride and triethylamine. The chloroacetylated material is then reacted with NaI in acetone to give the title compound.

Example H

Preparation of hexahydro-5-[(phenylmethoxy)amino]-2,5β-ethano-1H-3aα,6aα-cyclopenta[c]pyrrol-7-one

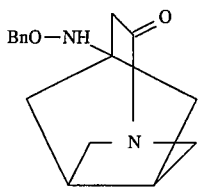

The title compound of example G is treated with tri-n-butylstannane in benzene at reflux containing a catalytic amount of AIBN. Upon workup the title compound is isolated.

Example J

Preparation of tetrahydro-2,5β-ethano-1H-3aα,6α-cyclopenta[c]pyrrole-5(3H)-amine

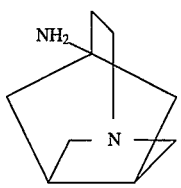

The title compound of example H is reacted with lithium aluminum hydride in tetrahydrofuran to afford after workup the title compound.

Example K

Preparation of 1,1-dimethylethyl hexahydro-5,5-bis(hydroxymethyl)cyclopenta[c]pyrrole-2(1H)-carboxylate

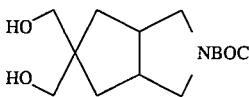

The starting material, 2-(1,1-dimethylethyl)5,5-dimethyl hexahydrocyclopenta[c]pyrrole-2,5,5-tricarboxylate, [For synthetic preparation of this material see Flynn, D. L. and Zabrowski, D. L., "Halogen Atom Transfer Annulations Involving Iodomalonates and Allylamine Derivatives" *Journal of Organic Chemistry*, 55, 1990, 3673–3674] is treated with gradual addition of lithium borohydride in tetrahydrofuran at room temperature. The solution is concentrated in vacuo washed in water and extracted into chloroform to afford the title compound in 95% yield. This material is used without further purification. ¹HNMR (300 MHz, CDCl₃): δ=1.32 ppm (m, 2H); 1.45 (s, 9H); 1.86 (m, 2H); 2.67 (m, 2H); 3.18 (m, 2H); 3.46 (m, 2H): 3.49 (d, 2H); 3.60 (d, 2H); 4.36 (d, 2H).

Example L

Preparation of 1,1-dimethylethyl hexahydro-5,5-bis[[[(4-methylphenyl)sulfonyl]oxy]methyl]cyclopenta[c]pyrrole-2(1H)-carboxylate

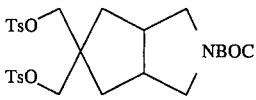

The diol compound prepared in Example K is dissolved in pyridine and treated with p-toluenesulfonyl chloride at −10° C., warmed to room temperature over two hours, diluted with aqueous sodium bicarbonate and extracted into chloroform to afford the title compound in 93% yield. This material is used without further purification. ¹HNMR (400 MHz, CDCl₃): β=1.26 ppm (m, 2H); 1.45 (s, 9H); 1.80 (m, 2H); 2.47 (s, 6H); 2.59 (m, 2H); 3.10 (d, 2H); 3.39 (dd, 2H); 3.78 (s, 2H); 3.85 (s, 2H); 7.36 (m, 4H); 7.72 (m, 4H).

Example M

Preparation of hexahydrocyclopenta[c]pyrrole-5,5(1H)-dimethanol,bis(4-methylbenzenesulfonate)

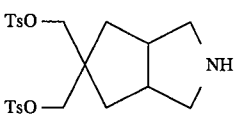

The carbamate prepared in Example L is treated with triflouroacetic acid, washed with aqueous potassium carbonate and extracted into chloroform to afford the title compound in 90% yield. This material is used without further purification. ¹HNMR (400 MHz, CDCl₃): δ=1.05 ppm (dd, 2H); 1.88 (dd, 2H); 2.19 (s, 1H); 2.45 (s, 3H); 2.46 (s, 3H); 2.49 (m, 2H); 2.65 (d, 2H); 2.73 (m, 2H); 4.82 (s, 2H); 4.87 (s, 2H); 7.33 (dd, 4H); 7.72 (m, 4H).

Example N

Preparation of hexahydro-2,5β-methano-1H-3aR, 3aα6aα-cyclopenta[c]pyrrole-5-methanol, 4-methylbenzenesulfonate

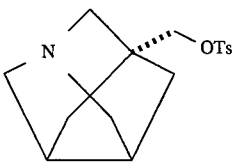

The bis tosylate prepared in Example M is dissolved in dimethylformamide, treated with cesium Carbonate and heated for 4 hours at 80° C. Dimethylformamide is removed by vacuum distillation and the residue washed with aqueous sodium hydroxide and extracted into chloroform to afford the title compound in 80% yield. This material is used without further purification. ¹HNMR (300 MHz, CDCl₃): δ=1.15 ppm (m, 4H); 2.46 (s, 3H); 2.59 (m, 2H); 2.75 (m, 1H); 2.79 (s, 2H); 2.80 (m, 1H); 2.87 (dd, 1H); 2.90 (dd, 1H); 3.72 (s, 2H); 7.34 (d, 2H); 7.76 (d, 2H).

Example P

Preparation of 5-(azidomethyl)hexahydro-2,5β-methano-1H-3aR,3aα,6α-cyclopenta[c]pyrrole

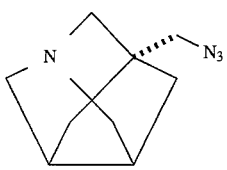

The azatricyclic tosylate prepared in Example N is dissolved in dimethylformamide treated with sodium azide and heated at 70° C for eight hours. After removal of dimethylformamide by vacuum distillation the residue is washed with aqueous sodium hydroxide and extracted into chloroform to yield crude product. The title compound is purified by silica gel chromatography eluting with ethanolic ammonia and chloroform resulting in 50% yield. $^1$HNMR (300 MHz, CDCl$_3$): δ=1.69 ppm (s, 4H); 2.63 (m, 2H); 2.85 (dd, 2H); 2.88 (s, 2H); 2.91 (s, 1H); 2.96 (s, 1H).

Example Q

Preparation of hexahydro-2,5β-methano-1H-3aR, 3aα,6aα-cyclopenta [c]pyrrole-5-methaneamine

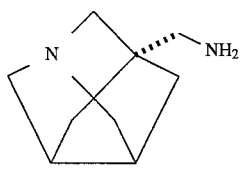

The azide prepared in Example P is dissolved in tetrahydrofuran and reduced with lithium aluminum hydride at reflux for two hours. After Feiser work up, *Reagents for Organic Synthesis* by Lewis F. Feiser and Mary Feiser, Vol. 1, p 584 (1967) John Wiley & Sons, and filtration the filtrate is concentrated under reduced pressure to afford the title compound in quantitative yield. This material is used without further purification. $^1$HNMR (300 MHz, CDCl$_3$): δ=1.63 ppm (m, 4H); 1.75 (m, 2H); 2.49 (s, 2H); 2.58 (quint, 2H); 2.82 (dd, 2H); 2.84 (s, 2H); 2.90 (s, 1H); 2.93 (s, 1H).

Example 1

Preparation of 4-amino-5-chloro-2-methoxy-N-(tetrahydro-1H-pyrrolizin-7a(5H)-ylmethyl)benzamide

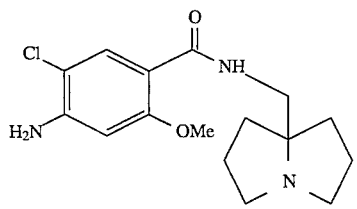

4-Amino-5-chloro-2-methoxybenzoic acid (134 mg, 0.00095 moles) and 1,1'-carbonyldi-imidazole (151 mg, 0.00095 moles) were suspended in the DMF (2.5 ml) and the mixture was stirred until solution occurred (three hours). At this time, tetrahydro-1H-pyrrolizin-7a(5H)-methylamine [amine J. Het Chem 24, 47, 1987](134 mg; 0.00095 moles) was added and the mixture was stirred for 2 hours. Tlc 30% MeOH/CHCl$_3$/1/10% NH$_4$OH indicated that the reaction was complete. Concentration afforded a residue which was purified by prep tlc chromatography, eluting with 15% MeOH/CHCl$_3$/1/10% NH$_4$OH to yield 73 mg (24%) of the product. The residue was converted to the HCl salt with MeOH/HCl.

| Elements | Calc | Found | |
|---|---|---|---|
| Carbon | 53.63 | 53.57 | C$_{16}$H$_{22}$ClN$_3$O$_2$ * 0.7 HCl * 0.5 H2O |
| Hydrogen | 6.67 | 6.66 | |
| Nitrogen | 11.73 | 11.54 | MW 358.35 |
| Chlorine | 16.82 | 16.51 | |

Example 1A

4-Amino-5-chloro-2-methoxy-N-(tetrahydro-1H-pyrrolizin-7a(5H)-ylethyl)benzamide

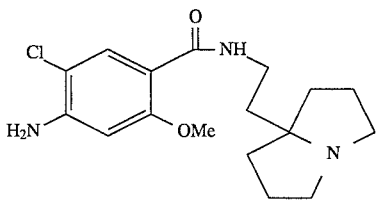

Procedure

4-Amino-5-chloro-2-methoxybenzoic acid (1.0 g, 0.005 moles) and 1,1'-carbonyldi-imidazole (892 mg, 0.00055 moles) were suspended in the DMF (10 ml) and the mixture was stirred until solution occurred (three hours). At this time, tetrahydro-1H-pyrrolizin-7a(5H)-ethylamine [amine Heterocycles 16, 755, 1981](771 mg; 0,005 moles) was added and the mixture was stirred for 1 hour. Tlc 30% MeOH/CHCl$_3$/1/10% NH$_4$OH indicated that the reaction was complete. Concentration afforded a residue which was partitioned between Et$_2$O/H$_2$O. The product crystallized. The solid was filtered and dissolved in CHCl$_3$, washed with dilute K$_2$CO$_3$, dried over MgSO$_4$ and concentrated to a solid. The solid was triturated with Et$_2$O and converted to the HCl salt with MeOH/HCl to yield 1.27g (69%) of the product.

| Carbon | 49.71 | 49.39 | C$_{17}$H$_{24}$ClN$_3$O$_2$ * 2 HCl |
|---|---|---|---|
| Hydrogen | 6.38 | 6.46 | |
| Nitrogen | 10.23 | 10.18 | MW 410.77 |
| Chlorine | 25.89 | 25.71 | |

Example 1B

N'-(tetrahydro-1H-pyrrolizin-7a(5H)-ylmethyl)-2-(2-propyloxy)phenylurea

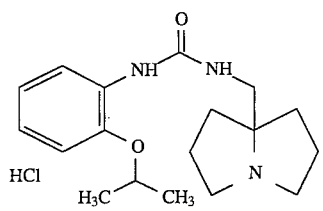

2-isopropoxy-aniline (123 mg, 0.813 mmole) was dissolved in CHCl₃ (1 ml), added triethyl amine (0.113 ml, 0.813 mmole). Cooled soln. to 0° C., added a solution of phosgene in toluene (0.458 ml, 0.927 mmole) and stirred for 1.5 hours. To this solution was added tetrahydro-1H-pyrrolizin-7a(5H)-methylamine (114 mgs, 0.813 mmole) in CHCl₃ and stirred for 18 hours. Solvent removed via rotary evaporator to give crude product as a solid. Solid was chromatographed on silica gel eluting with 5% CH₃OH(NH₃↑)/CHCl₃ to give 220 mg (85%) of title compound as free base.

| Calculated for $C_{18}H_{27}N_3O_2$: | Found |
|---|---|
| C, 67.89 | 67.96 |
| H, 8.86 | 8.61 |
| N, 13.19 | 12.96 |
| Calculated MS for $C_{18}H_{23}N_3O_2$ | = 318.44 |
| Found M | = 318.215 |

Example 2

Preparation of N-(tetrahydro-1H-pyrrolizin-7a(5H)-ylmethyl)-1H-indole-3-carboxamide

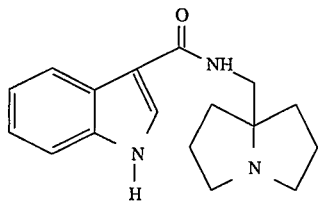

Following the procedure of example 1, 7a-Aminomethylhexahydro-1H-pyrrolizine is reacted with indole-3-carboxylic acid to afford the title compound.

Indole-3-carboxylic acid (161 mg, 0.001 moles) and 1,1-carbonyldiimidazole (162 mg, 0.001 moles) were suspended in the DMF (2.5 ml) and the mixture was stirred until solution occurred (three hours). At this time, tetrahydro-1H-pyrrolizin-7a(5H)-methylamine [amine J. Het Chem 24, 47, 1987] (140 mg; 0,001 moles) and triethylamine (560 μl; 0,004 mole) were added and the mixture was stirred for 1 hour. Tlc 30% EtOH/CHCl₃/1/10% NH₄OH indicated that the reaction was complete. Concentration afforded a residue that was partitioned between Et₂O/H₂O . The product crystallized. The solid was filtered and dissolved in CHCl₃, washed with dilute NaOH, dried over MgSO₄ and concentrated to a solid. The solid was triturated with Et₂O and converted to the HCl salt with MeOH/HCl to yield 174 mg (62%) of the product.

| Elements | Calc | Found | |
|---|---|---|---|
| Carbon | 62.98 | 62.68 | $C_{17}H_{21}N_3O$ * 0.75 HCl * 0.75 H₂O |
| Hydrogen | 7.23 | 6.68 | |
| Nitrogen | 12.96 | 12.96 | MW 324.23 |
| Chlorine | 8.20 | 8.31 | |

Example 3

Preparation of 2,3-dihydro-N-(tetrahydro-1H-pyrrolizin-7a(5H)-ylmethyl)-1H-indole-1-carboxamide

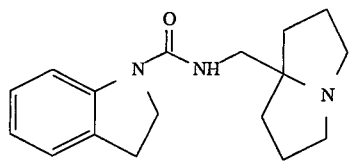

7a-Aminomethylhexahydro-1H-pyrrolizine is reacted with indoline-N-trichloromethylcarbamate [J. Medicinal Chemistry (1990) 33: 1929] in toluene at reflux to afford the title compound after extractive workup and column chromatography.

Example 4

Preparation of 1-methyl-N-(tetrahydro-1H-pyrrolizin-7a(5H)-ylmethyl)-1H-indazole-3-carboxamide

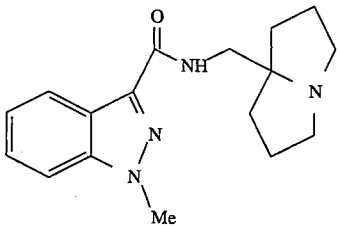

Following the procedure of example 1, 7a-Aminomethylhexahydro-1H-pyrrolizine is reacted with N-methylindazole-3-carboxylic acid [J. Medicinal Chemistry (1987) 30: 1535] to afford the title compound.

Example 5

Preparation of 4-amino-5-chloro-2-methoxy-N-(tetrahydro-2,5β-methano-1H-3aα,6aα-cyclopenta[c]pyrrol-5 (3H)-yl)benzamide

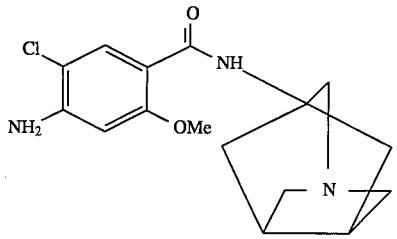

N-hexahydro-1H-2,5β-methano-3aα,6aα-cyclopenta[c]pyrrol-5α-amine is reacted with 2-methoxy-4-amino-5-chlorobenzoic acid and carbonyldiimidazole in dimethylformamide to afford the title compound.

Example 6

Preparation of N-(tetrahydro-2,5β-methano-1H-3aα,6aα-cyclopenta[c]pyrrol-5(3H)-yl)-1H-indole-3-carboxamide

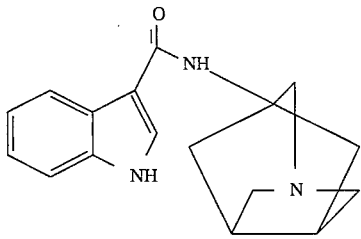

N-hexahydro-1H-2,5β-methano-3aα,6aα-cyclopenta[c]pyrrol-5aα-amine is reacted with indole-3-carboxylic acid according to the procedure of example 5 to afford the title compound.

Example 7

Preparation of 1-methyl-N-(tetrahydro-2,5β-methano-1H-3aα,6αa-cyclopenta[c]pyrrol-5(3H)-yl)-1H-indazole-3-carboxamide

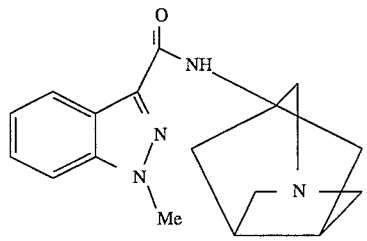

N-hexahydro-1H-2,5β-methano-3aα,6aα-cyclopenta[c]pyrrol-5α-amine is reacted with N-methylindazole-3-carboxylic acid according to the procedure of example 5 to afford the title compound.

Example 8

Preparation of 2,3-dihydro-N-(tetrahydro-2,5β-methano-1H-3aα,6aα-cyclopenta[c]pyrrol-5(3H-yl)-1H-indole-3-carboxamide

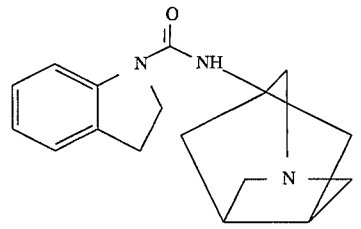

N-hexahydro-1H-2,5β-methano-3aα,6aα-cyclopenta[c]pyrrol-5α-amine is reacted with indoline-N-trichloromethylcarbamate according to the procedure of example 3 to afford the title compound.

Example 9

Preparation of 4-amino-5-chloro-N-[(hexahydro-2,5β-methano-1H-3aR,3aα,6aα-cyclopenta[c]pyrrol-5-yl)methyl]-2-methoxybenzamide

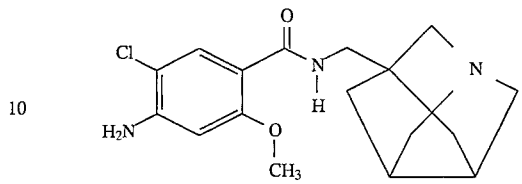

A solution of 2-methoxy-4-amino-5-chlorobenzoic acid in dimethylformamide is treated with 1,1-carbonyldiimidazole and the resultant imidazolide is reacted with hexahydro 2,5β-methano-1H-3aα,6aα-cyclopenta[c]pyrrole-5 (3H) -methaneamine. The mixture is chromatographed on silica gel eluting with ethanolic ammonia and chloroform to afford the title compound in 56% yield. $^1$HNMR (400 MHz, CDCl$_3$): δ=1.70 ppm (m, 4H); 2.60 (quint, 2H); 2.82 (dd, 2H); 2.88 (s, 2H); 2.90 (s, 1H); 2.95 (s, 1H); 3.29 (d, 2H); 3.91 (s, 3H); 4.45 (s, 2H); 6.31 (s, 1H); 7.65 (t, 1H); 8.10 (s, 1H).

Example 10

Preparation of N-[(hexahydro-2,5β-methano-1H-3aR,3aα,6α-cyclopenta[c]pyrrol-5-yl)methyl]-1H-indole-3-carboxamide

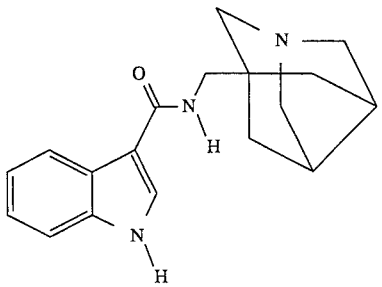

Indole-3-carboxylic acid is converted to the acid chloride intermediate in refluxing thionyl chloride and methylene chloride. After azeotroping excess thionyl chloride with toluene this acid chloride intermediate is reacted with hexahydro-2,5β-methano-1H-3aR,3aα,6aα-cyclopenta[c] pyrrole-5-methaneamine in triethylamine and chloroform and chromatographed on silica gel eluting with ethanolic ammonia and chloroform to afford the title compound in 18% yield. $^1$HNMR (300 MHz, CDCl$_3$): δ=1.70 ppm (m, 4H); 2.60 (quint, 2H); 2.82 (dd, 2H); 2.88 (s, 2H); 2.90 (s, 1H); 2.95 (s, 1H); 3.30 (d, 2H); 6.32 (t, 1H); 7.22 (dd, 2H); 7.39 (dd, 1H); 7.80 (m, 1H); 7.93 (m, 1H).

A. In Vitro Functional Assay for Serotonin 5-HT$_4$ agonism: RAT TMM

Serotonin 5-HT$_4$ agonism was measured in the rat esophagus in vitro preparation as reported by Baxter et al (Naunyn. Schmied. Arch. Pharmacol. 1991, 343,439). Agonist activity was determined utilizing relaxation of carbachol-contracted rat tunica muscularis mucosae. One 2 cm segment of intrathoracic esophagus proximal to the diaphragm was removed from male rats, weighing approximately 300 gm, and the outer muscle layers removed. The inner tunica muscularis mucosa was mounted under 0.2–0.3 g of tension in a tissue bath containing oxygenated Tyrode's solution at 37° C. Cortisterone acetate (30 μM) and fluoxetine (1 μM) were included in the buffer to prevent uptake of serotonin, as well as pargyline (10 μM) to inhibit monoamine oxidase. Following a 30 min equilibrium period, tissues were isometrically contracted with carbachol (3 μM) to obtain a tonic contraction. A stable plateau was obtained within 20 min when test compound was added cumulatively to relax the muscle strip. $EC_{50}$ values were obtained for each agonist in tissues from 5 rats. $EC_{50}$ values for agonists at this $5\text{-}HT_4$ receptor are indicated as follows for the indicated compounds:

Example 1  422 nM
Example 9  216 nM

The compounds herein exhibit 5-HT3 antagonism. 5-HT3 antagonism can be determined by the radioligand receptor binding assay as described herein and in the in vivo Bezold-Jarisch reflex procedure.

Serotonin ($5\text{-}HT_3$)

Procedure

GR65630 binds to the $5\text{-}HT_3$ receptor. Brain cortices are obtained from male rats and a membrane fraction prepared by standard techniques. 0.04 mg of membrane prep is incubated with 0.2 nM [$^3$H]-GR656630 for 60 minutes at 22° C. Non-specific binding is estimated in the presence of 1 uM ICS 205–930. Membranes are filtered and washed 3 times and the filters are counted to determine [3H]-GR65630 specifically bound.*

*Literature Reference
Kilpatrick G J, Jones B J and Tyers M B. Identification and distribution of $5\text{-}HT_3$ receptors in rat brain using radioligand binding. Nature, 330: 746–748, 1987.

Results

Kd=2.46 nM
Bmax=154 fmol/mg protein
% Specific Binding: 70

| Effect of Reference Compounds on [H]-GR65630 Bound (0.2 nM) | | | |
|---|---|---|---|
| Compound | $IC_{50}$ | Ki | Hill Coefficient |
| Quipazine | 0.5 nM | 0.18 nM | 0.86 |
| ICS 205-930 | 2.2 nM | 0.51 nM | 1.0 |
| 5-HT | 122 nM | 0.39 uM | 1.0 |
| RU24969 | 320 nM | 1.85 uM | 1.0 |
| Zacopride | 0.55 nM | 0.18 nM | 0.86 |

Bezold-Jarisch Reflex

The test sample is administered i.p. (mg/kg) to a group of 3 mice. Thirty minutes later, a 5-HT (0.25 mg/kg i.v.)-induced bradycardia is recorded in pentobarbital anesthetized animals. A greater than 50 percent (>50) reduction in the bradycardic response relative to vehicle-treated control mice is considered significant.

| REFERENCE AGENTS: | Minimum Effective Dose (MED) mg/kg |
|---|---|
| BRL-43694 | 0.05 |
| cisapride | 5 |
| cyproheptadine | 5 |
| domperidone | >10 |
| GR-38032 | 0.5 |
| ketanserin | >10 |
| mecamylamine | 2.5 |
| methysergide | >10 |
| metoclopramide | 5 |
| scopolamine | 2.5 |

This method has been described by Saxena, P. R. and Lawang, A., Arch. Int. Pharmacodyn., 277: 235–252, 1985.

Also embraced within this invention is a class of pharmaceutical compositions comprising one or more of the described compounds in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents,

What is claimed is:

1. A compound of the formula

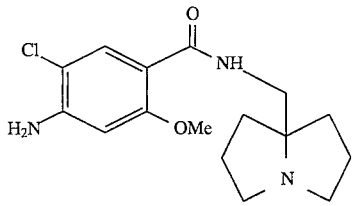

a stereoisomer or pharmaceutically acceptable salt thereof.

2. A pharmaceutical composition for treatment of anxiety, psychoses, depression, gastrointestinal motility disturbances or conditions responsive to 5-$HT_3$ antagonist effect comprising a therapeutically effective amount of a compound of the formula

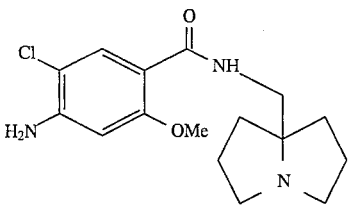

and a pharmaceutically acceptable carrier or diluent.

* * * * *